(12) United States Patent
Johnson et al.

(10) Patent No.: US 10,864,096 B2
(45) Date of Patent: Dec. 15, 2020

(54) THREE-DIMENSIONAL THIN-FILM NITINOL DEVICES

(71) Applicant: Monarch Biosciences, Inc., Los Angeles, CA (US)

(72) Inventors: Alfred David Johnson, San Leandro, CA (US); Colin Kealey, Los Angeles, CA (US)

(73) Assignee: MONARCH BIOSCIENCES, INC., Los Angeles, CA (US)

(*) Notice: Subject to any disclaimer, the term of this patent is extended or adjusted under 35 U.S.C. 154(b) by 0 days.

(21) Appl. No.: 16/298,758

(22) Filed: Mar. 11, 2019

(65) Prior Publication Data

US 2019/0201220 A1 Jul. 4, 2019

Related U.S. Application Data

(60) Division of application No. 15/136,809, filed on Apr. 22, 2016, now abandoned, which is a continuation of
(Continued)

(51) Int. Cl.
*A61F 2/90* (2013.01)
*A61F 2/86* (2013.01)
(Continued)

(52) U.S. Cl.
CPC .............. *A61F 2/90* (2013.01); *A61F 2/844* (2013.01); *A61F 2/86* (2013.01); *A61L 31/088* (2013.01);
(Continued)

(58) Field of Classification Search
CPC .... A61F 2/90; A61F 2/844; A61F 2/86; A61F 2240/001; A61F 2210/0076;
(Continued)

(56) References Cited

U.S. PATENT DOCUMENTS 5,242,759 A * 9/1993 Hall ..................... B23K 35/004
228/207
6,746,890 B2 * 6/2004 Gupta .............. A61B 17/12022
438/50
(Continued)

FOREIGN PATENT DOCUMENTS

WO  WO 2005/122714  12/2005
WO  WO 2014/131037  8/2014

OTHER PUBLICATIONS

Chun et al, Proc of SPIE, vol. 7650, 7650T, 2010, Health Monitoring of Structural and Biological Systems 2010, edited by Tribikrann Kundu, "Micro Patterning Processes for Thin Film Nitinol Endografts and Evaluation of Endothelialization in Swine Model". (Year: 2010).*

(Continued)

*Primary Examiner* — Anita K Alanko
(74) *Attorney, Agent, or Firm* — Haynes and Boone, LLP

(57) ABSTRACT

A method of manufacturing three-dimensional thin-film nitinol (NiTi) devices includes: depositing multiple layers of nitinol and sacrificial material on a substrate. A three-dimensional thin-film nitinol device may include a first layer of nitinol and a second layer of nitinol bonded to the first layer at an area masked and not covered by the sacrificial material during deposition of the second layer.

7 Claims, 7 Drawing Sheets

Related U.S. Application Data application No. PCT/US2014/061836, filed on Oct. 22, 2014.

(60) Provisional application No. 61/896,541, filed on Oct. 28, 2013, provisional application No. 61/894,826, filed on Oct. 23, 2013.

(51) Int. Cl.
| | |
|---|---|
| *A61L 31/08* | (2006.01) |
| *C23C 14/00* | (2006.01) |
| *C23C 14/04* | (2006.01) |
| *C23C 14/16* | (2006.01) |
| *A61F 2/844* | (2013.01) |
| *C23C 14/34* | (2006.01) |
| *C23C 14/58* | (2006.01) |
| *A61F 2/06* | (2013.01) |
| *C23F 1/44* | (2006.01) |
| *B81C 1/00* | (2006.01) |
| *A61F 2/82* | (2013.01) |

(52) U.S. Cl.
CPC ........ *C23C 14/0005* (2013.01); *C23C 14/042* (2013.01); *C23C 14/165* (2013.01); *C23C 14/34* (2013.01); *C23C 14/5846* (2013.01); *A61F 2/06* (2013.01); *A61F 2002/068* (2013.01); *A61F 2002/823* (2013.01); *A61F 2210/0014* (2013.01); *A61F 2210/0076* (2013.01); *A61F 2230/0017* (2013.01); *A61F 2230/0069* (2013.01); *A61F 2240/001* (2013.01); *B81C 1/00476* (2013.01); *C23F 1/44* (2013.01)

(58) Field of Classification Search
CPC ...... A61F 2230/0069; A61F 2230/0017; A61F 2002/823; A61F 2/06; A61F 2210/0014; A61F 2002/068; C23C 14/165; C23C 14/042; C23C 14/0005; C23C 14/5846; C23C 14/34; A61L 31/088; B81C 1/00476; C23F 1/44

See application file for complete search history.

(56) References Cited

U.S. PATENT DOCUMENTS

| | | |
|---|---|---|
| 6,790,298 B2 | 9/2004 | Johnson et al. |
| 8,216,931 B2 | 7/2012 | Zhang |
| 8,715,335 B2 | 5/2014 | Palmaz et al. |
| 2004/0014253 A1 | 1/2004 | Gupta et al. |
| 2006/0059705 A1* | 3/2006 | Wang ............... B01D 53/28 |
| | | 34/72 |
| 2008/0125848 A1 | 5/2008 | Kusleika et al. |
| 2011/0056909 A1 | 3/2011 | Sims et al. |

OTHER PUBLICATIONS

Chun et al., "Micro Patterning Processes for Thin Film Nitinol Endografts and Evaluation of Endothelialization in Swine Model," Proceedings of the SPIE, Mar. 8, 2010, pp. 76502T1-76502T11, vol. 7650, The International Society for Optical Engineering SPIE, Bellingham, WA, USA.

Hahnlen et al., "Ultrasonic Soldering of Shape Memory NiTi to Aluminum 2024," Welding Journal, Jan. 1, 2012, pp. 1s-7s, vol. 91—No. 1, American Welding Society, Miami, FL, USA.

Rigberg et al., "Thin-film nitinol (NiTi): A feasibility study for a novel aortic stent graft material," Journal of Vascular Surgery, Aug. 2009, pp. 375-380, vol. 50, No. 2, Society for Vascular Surgery, Santa Monica, CA, United States.

PCT International Search Report and Written Opinion of the International Application No. PCT/US2014/061836, 9 pages, dated Mar. 24, 2015.

Extended European Search Report in International Application No. PCT/US2014/061836, 14 pages, dated Sep. 1, 2017.

* cited by examiner

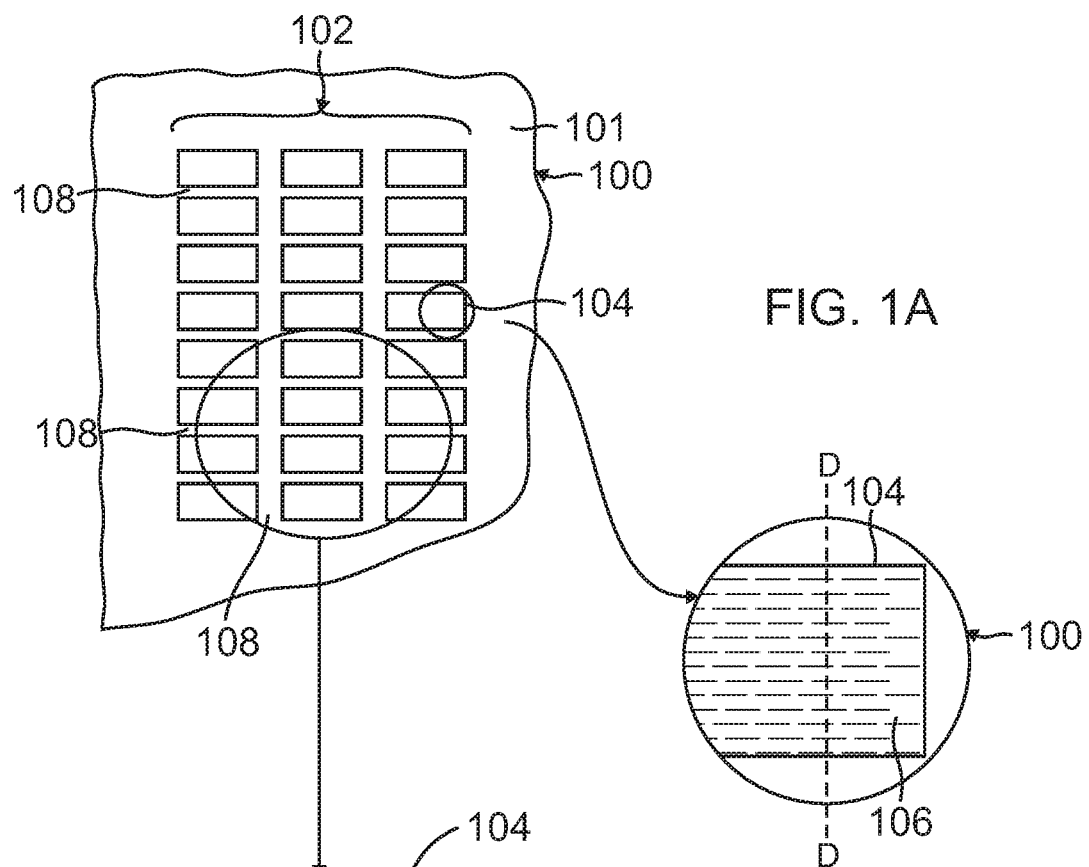
FIG. 1A
FIG. 1B
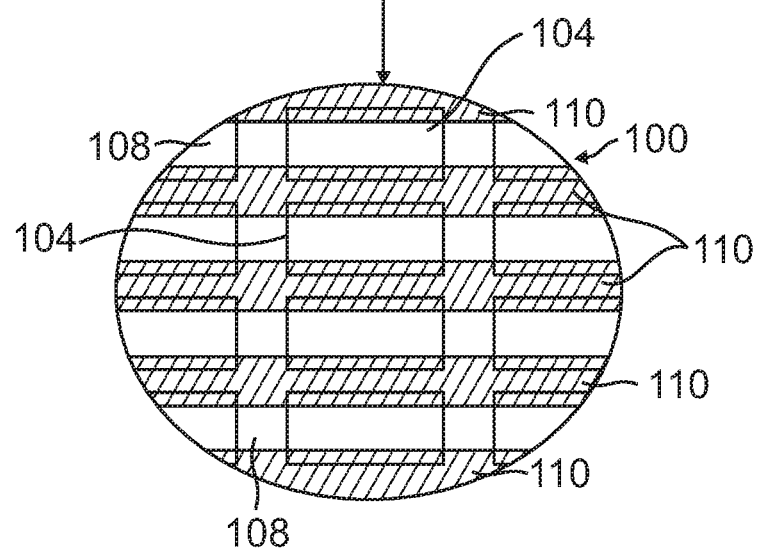
FIG. 1C

THREE-DIMENSIONAL THIN-FILM NITINOL DEVICES

RELATED APPLICATIONS

This application is a divisional application of U.S. patent application Ser. No. 15/136,809, filed Apr. 22, 2016, and entitled "THREE-DIMENSIONAL THIN-FILM NITINOL DEVICES," which is a continuation of International Patent Application No. PCT/US2014/061836, filed Oct. 22, 2014, and entitled "THREE-DIMENSIONAL THIN-FILM NITINOL DEVICES," which claims the benefit of U.S. Provisional Application No. 61/894,826, filed Oct. 23, 2013, and entitled "SPUTTERED TiNi THIN FILM," and U.S. Provisional Application No. 61/896,541, filed Oct. 28, 2013, and entitled "THREE-DIMENSIONAL THIN-FILM NITINOL DEVICES," which are all hereby incorporated by reference in their entirety.

STATEMENT REGARDING FEDERALLY SPONSORED RESEARCH OR DEVELOPMENT

This invention was made with government support under NIH grant 1-R41-NS074576-01 awarded by the National Institutes of Health (NIH). The government has certain rights in the invention.

TECHNICAL FIELD

The present disclosure generally relates to intravascular devices and, more particularly, to production, using Nitinol thin-film techniques, of devices used for treatment of intracranial aneurysm.

BACKGROUND

There is a relatively narrow band of temperature in which nitinol can be mechanically stressed so as to transition at least partially into the martensite phase from the austenite phase despite being above the transformation temperature. This property of nitinol is referred to as superelasticity and is quite advantageous in that—as the name suggests—superelastic nitinol is very flexible compared to conventional metal alloys. If the stress is removed and the nitinol is above the transformation temperature, the nitinol will revert back to the austenite phase and assume its unstressed original shape. For example, a cylindrical nitinol stent may be deformed into the superelastic state so that it can be packaged and delivered into a blood vessel using a catheter. As the stent is released from the catheter, the stent reverts to its original cylindrical shape in the blood vessel. Nitinol is thus also denoted as a shape memory alloy.

In one application, nitinol may be used to construct neurovascular flow diverter nitinol stents that may be placed in blood vessels in the region of a cerebral aneurysm. The flow diverter stent essentially takes the shape of the blood vessel prior to the formation of the aneurysm, which is then cutoff from the blood flow. The blood within the diverted aneurysm clots, which neutralizes the aneurysm. Although such flow diverter therapy shows great promise, its application is extremely challenging. The affected cerebral vessels may be very small—for example, a vessel to be stented may have a diameter of just three millimeters such that they are very delicate and prone to rupture. Balloon expanded stents are thus too risky for neurovascular applications. In contrast, a superelastic nitinol stent is far safer and is also biocompatible.

To choke off the aneurysm, flow diverter stents are sheathed in a flow diverter cover. The cover has to satisfy two opposing goals. On the one hand, the cover should inhibit blood flow into the aneurysm so that its blood pools and thereby clots. A completely sealed cover would thus best satisfy such a goal. On the other hand, the aneurysm may be adjacent to various feeder vessels that branch off from the area to be stented. If these feeder vessels are choked off by the flow diverter stent cover, the patient may suffer an ischemic stroke, a potentially catastrophic complication. To achieve these conflicting goals, the flow diverter cover may comprise a fine wire mesh made from a thin film nitinol (for example, 50 microns or less in thickness) to allow blood to escape from the flow diverter stent into any feeder vessels that would otherwise be occluded. Fine-wire-mesh thin-film flow diverter nitinol stent covers with perforations of 100 to 300 microns in length offer great promise. The "wire" in the fine wire mesh should be quite thin (for example, 5 to 20 microns in diameter) because it is the edges of the wire that assist in the flow diverting effect. But it is very challenging to form a fine wire mesh thin film cylindrical nitinol stent cover.

In particular, thin film nitinol is conventionally manufactured by being sputtered onto a suitable substrate such as silicon. The sputtering is problematic, however, in that the resulting thin film nitinol is prone to having an undesirable crystalline structure as opposed to a desired amorphous state. An amorphous film can be crystallized by heating to approximately 500° C. in a process known as annealing. Such a crystalline structure is essential to achieving the austenite-to-martensite phase change that is the hallmark of a shape memory alloy. But conventional sputtering techniques will often form a thin film having a columnar crystalline structure. The columns are only loosely bound with each other such that the resulting film is quite brittle and unsuitable. Accordingly, there is a need in the art for improved thin film nitinol manufacturing techniques that can reliably form high-quality amorphous thin film that may be subsequently crystallized through annealing.

Setting aside the difficulties with regard to forming amorphous thin film nitinol, it is desirable that the resulting stent cover formed from suitable thin film nitinol be fenestrated as discussed earlier. To form openings in the thin film, it is conventional to etch the film using photolithographic techniques. The resulting opening can then be expanded by stretching the etched thin film nitinol to fully open up the desired fenestrations such that the film forms a wire mesh analogous to a chain-link fence except that there is no weaving of the resulting wire mesh. The wire mesh may be relatively thin in comparison to the fenestrations. For example, the fenestrations may have a length of approximately 300 microns whereas the wire itself may be just 20 across or even thinner. The resolution of wet etching is relatively coarse such that if the wire mesh is etched to the desired thinness (for example, 5 to 20 microns in diameter), the mesh is then prone to tearing and other flaws. The resolution of wet etching is relatively coarse such that if the wire mesh is etched to the desired thinness (for example, 5-20 microns in diameter), the mesh is then prone to tearing and other flaws.

The substrate upon which the nitinol is sputtered includes a release layer so that the etched thin film nitinol can be removed from the substrate. But the etched thin film nitinol is essentially two dimensional (if one ignores the third dimension resulting from its relatively small thickness). This two-dimensional thin film must be sealed onto itself in some fashion to form a cylinder or other type of three-dimensional structure. To seal one edge of the thin film to another edge, it was known to use glue or stitching. But nitinol bonds poorly with glue. Similarly, stitching opposing edges together is also problematic given the relatively tiny dimensions of the resulting wire mesh.

Given the difficulties with joining layers of nitinol to form a three-dimensional structure, it is also known to deposit nitinol onto a cylindrical mandrel to form a cylindrical nitinol film. But such deposition is not amenable to mass production as the mandrel results in just one cylindrical structure. In contrast, conventional planar techniques can mass produce assorted cylindrical structures simultaneously across a wafer substrate. In addition, deposit onto mandrel produces a solid film that must then be fenestrated upon removal from the mandrel. The resulting cylindrical structure is not amenable to photolithographic etching so it is fenestrated using a laser, which results in relatively coarse features. Accordingly, there is a need in the art for improved techniques for manufacturing fine wire mesh thin film nitinol three-dimensional structures.

BRIEF DESCRIPTION OF THE DRAWINGS

FIG. 1A is a plan view diagram illustrating a portion of a silicon wafer substrate and associated structures, in accordance with an embodiment of the present disclosure.

FIG. 1B is a more detailed view of a portion of FIG. 1A as indicated.

FIG. 1C is a more detailed view of another portion of FIG. 1A as indicated.

Figure 1D:
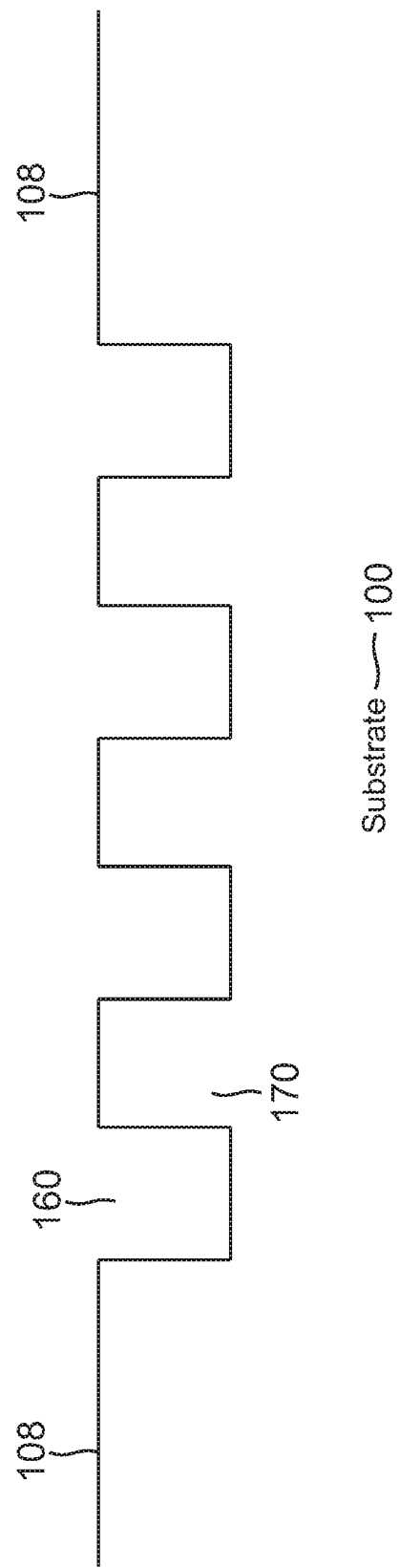
FIG. 1D is a cross-sectional view of the silicon wafer substrate of FIG. 1B along dashed line D prior to deposition of the nitinol layer.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

The techniques and structures disclosed herein achieve economical, large-scale production of cylindrical nitinol film structures at reasonable cost. To provide low-cost mass production, nitinol film is sputtered deposited onto a semiconductor wafer substrate. In the prior art, the resulting film was etched using photolithographic techniques to form the desired fenestrations. In contrast, the film disclosed herein is sputtered deposited onto a substrate having dry-etched trenches formed using deep reactive ion etching (DRIE) techniques. The substrate trenches correspond to the desired fenestrations in the resulting thin film nitinol deposited onto the etched substrate. Deep reactive ion etching of the substrate is quite advantageous as compared to conventional wet etching techniques to form the fenestrations. For example, deep reactive ion etching is considerably more precise and thus enables the formation of features with as little as one micron accuracy. In addition, the wet etching techniques left residue on the nitinol film that interfered with joining to another film so as to construct a three-dimensional structure such as a cylindrical stent cover. In contrast, deep reactive ion etching of the substrate is entirely separate from the subsequent deposition of the nitinol film and thus causes no contamination of the film.

After the film has been sputtered onto patterned silicon wafers, it may be removed using a lift-off process by etching away a sacrificial layer such as a chromium layer. Combining this lift-off process with multiple-layer depositions of nitinol separated by layers of sacrificial material enables fabrication of cylindrical stent covers, which are three-dimensional in the sense that two layers are joined together along their longitudinal edges such that the resulting joined layers may be opened up to form a cylinder.

The patterned substrate is prepared by deposition of a chrome lift-off layer. Upon deposition of a first nitinol film onto the chrome lift-off layer, a chrome sacrificial layer may be deposited through a mask onto the first nitinol film. The mask covers substantially all of the patterned area of the substrate except for the longitudinal edges along which the first nitinol film is to be joined to a second film. The subsequent deposition of a second nitinol film then covers both the chrome sacrificial layer and the unmasked longitudinal edges of the first nitinol layer. The completed mesh may be removed from the substrate by etching of the chrome lift-off layer and the sacrificial chrome layer. A mandrel may be used to shape-set the mesh into the desired cylindrical form by heating to annealing temperature.

A major problem is solved herein with respect to the deposition of the second nitinol layer. In particular, note that nitinol will promptly form an oxidized surface layer upon exposure to the atmosphere. This oxidized layer is quite resistant to bonding to additional nitinol layers. To prevent formation of the oxidized layer, one could thus mask the first nitinol layer and deposit the sacrificial chrome layer, and remove the mask and deposit the second nitinol layer while maintaining a vacuum during the entire process. But such a procedure is of course very cumbersome with regard to aligning the mask and then removing it while maintaining a vacuum during the procedure. A particularly advantageous aluminum bonding layer is disclosed herein that obviates the need for maintaining a vacuum over all the manufacturing steps. In that regard, the first nitinol layer may be deposited (which of course is done in a vacuum chamber) but the vacuum may be released while the mask is applied. The subsequent deposition of the sacrificial chrome layer is performed in the vacuum chamber. The mask may then be removed without maintaining the vacuum and a reverse mask applied. As implied by the name, the reverse mask would be the complement of the mask used to deposit the chrome sacrificial layer. The reverse mask thus exposes the longitudinal edges of the first nitinol layer along which it is to bond to the yet-to-be deposited second nitinol layer so that these edges may be covered with an aluminum layer.

Upon deposition of the aluminum layer, the second nitinol layer may be sputtered deposited in the vacuum chamber. The two nitinol layers are thus separated by the aluminum layer along the longitudinal edges where the two nitinol layers are to be joined. This aluminum layer is quite advantageous as the resulting structure may be heated to approximately 500 to 600 degrees Celsius so that the aluminum partially melts. As opposed to the oxidized aluminum surfaces, the molten aluminum is very chemically reactive and actively bonds to both nitinol layers. In this fashion, the two nitinol layers are bonded together despite the formation of an oxidized layer on the first nitinol layer. The ability to break the vacuum so as to assist in the mask alignment and other steps greatly lowers manufacturing costs. In addition, the chemical bonding of the aluminum layer to the two nitinol layers provides a very secure bond. As discussed earlier, the conventional alternative was to glue or stitch the two layers together, which is quite unsatisfactory from both a production viewpoint as well as with regard to biocompatibility issues of the glue or problems caused by the stitching.

The deposition of the nitinol layers themselves is problematic. It was conventional for the nitinol layers to be undesirably brittle from the formation of a columnar crystalline structure. Alternatively, the nitinol may be deposited so as to have an undesirable tensile strain that can actually crack or break the substrate surface from the resulting tensile forces. Applicant has discovered that a very narrow range of manufacturing parameters results in high-quality film. In contrast, manufacture outside of these parameters results in excessively brittle material or undesirable tensile strain. With regard to these parameters, the sputtering power, the distance between the sputtering target and the substrate, and Ar pressure are critical as will be discussed further herein.

Figure 2:
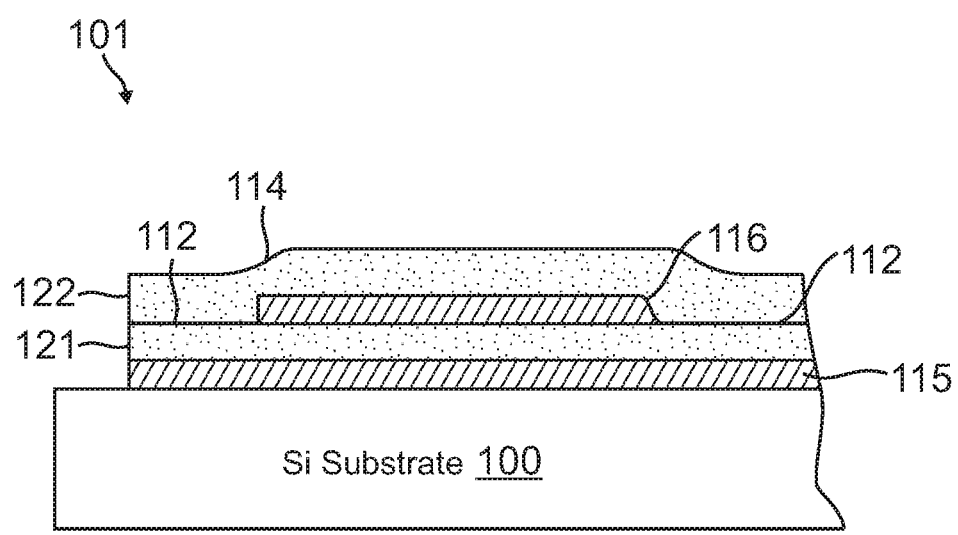
FIG. 2 is a cross sectional view diagram showing a portion of a silicon wafer substrate and structures, in accordance with one embodiment.
Figure 3:
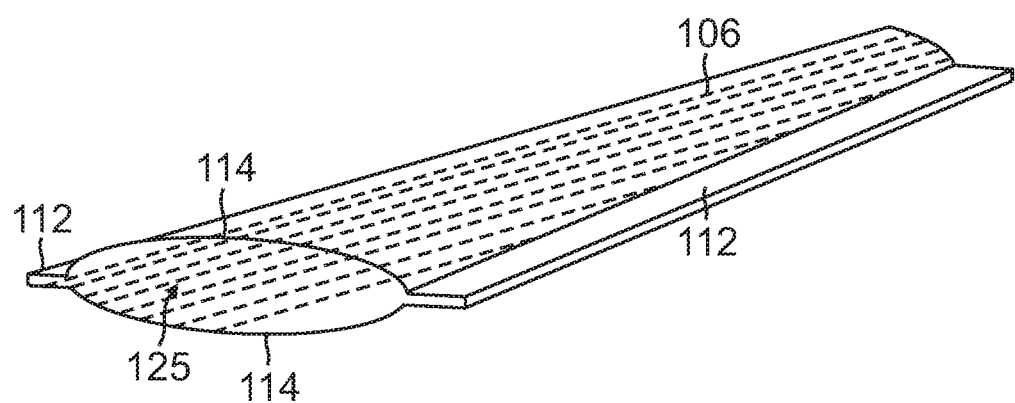
FIG. 3 is a perspective view diagram showing an example of a structure formed on a silicon wafer substrate, in accordance with an embodiment.

FIGS. 1A, 1B, 1C, and 1D illustrate a portion of a silicon wafer substrate 100 in accordance with one or more embodiments. As shown in FIG. 1A, a thin film layer 101 may be deposited on, for example, a silicon substrate 100 using sputtering. Since the surface of the substrate is planar, the resulting thin film layer 101 is also planar. As seen in the cross-sectional view of FIG. 2, layer 101 comprises a lift-off layer 115 that is initially deposited onto the surface of substrate 100. A first NiTi layer 121 covers lift-off layer 115. This first NiTi layer 121 forms one-half of a resulting stent cover (not illustrated). The remaining half of the stent cover is formed by a second NiTi layer 122 that is partially separated from first NiTi layer 121 by a sacrificial layer 116. Sacrificial layer 116 forms what will eventually become the lumen of the resulting stent cover. NiTi layers 121 and 122 are not joined together along the longitudinal edges of the resulting stent cover and thus along the longitudinal edges of sacrificial layer 116. These longitudinal edges 112 are shown in FIG. 3 after removal of the sacrificial layer 116 to form a stent cover 114. A lumen 125 for stent cover 114 exists in the place of the removed sacrificial layer 116.

To function as stent cover for neurological applications, stent cover 114 should have fenestrations 106. Referring again to FIG. 1A, substrate 100 may be configured so that thin film layer 101 includes the patterns of fenestrations 104 for each subsequently formed stent cover. These patterns of fenestrations 104 may also be denoted as a fiche 104 in that the fenestrations 104 are in collapsed form on substrate 100. Just like a microfiche, each fiche 104 or pattern of fenestrations effectively codes for the resulting fenestrations when the stent cover is expanded to fully open up the fenestrations. The number of fiches 104 on substrate 100 thus determines the resulting number of stent covers 114 that will be produced in one given production batch.

A close-up view of a fiche 104 is shown in FIG. 1B. Fenestrations 104 at this stage are not expanded and thus are in the form of narrow columnar apertures. One column of apertures is staggered with regard to an adjacent column so that when the fenestrations 104 are later expanded, the resulting stent cover has a "chain link fence" mesh pattern. As will be explained further herein, such a mesh pattern is quite advantageous for a flow diverter stent cover.

FIG. 1D shows a cross-sectional view of the fiche 104 of FIG. 1B. But in FIG. 1D, thin film layer 101 has not yet been formed. To form the desired fenestrations that make up a fiche or pattern of fenestrations, substrate 100 includes corresponding grooves 160 formed using a deep reactive ion etching process. Lands 170 support the subsequent thin film layer 101 that will form a wire mesh between adjacent fenestrations. Referring again to FIG. 1B, each fenestration 104 (prior to being expanded) may be approximately 5 to 20 microns across and approximately 300 microns in length. Each land 170 may also be approximately 5 to 20 microns across. Such a land width means that the resulting wire mesh will also have a width of approximately 5 to 20 microns across. The wire depth depends upon the film layer 101 depth, which may be, for example, from 5 to 20 microns in depth. It will be appreciated, however, that these dimensions are just examples and may be varied in alternate embodiments.

Trenches or grooves 160 may be 50 microns deep in one embodiment. Following removal of lift-off layer 115 and sacrificial layer 116, NiTi layers 121 and 122 may be crystallized at 500° deg. C. for about 120 minutes in a vacuum less than $1 \times 10^{-7}$ Torr, which may produce, for example, a 6 micron thick micropatterned Nitinol thin film sheet (e.g., device component 114) that can be lifted off the silicon substrate (e.g., silicon wafer substrate 100).

In one embodiment, the DC sputtering process involves the use of a near equiatomic NiTi alloy target under ultra-high vacuum (UHV) atmosphere (e.g., base pressure of a sputter chamber may be set below $5 \times 10^{-8}$ Torr and argon (Ar) pressure about $1.5 \times 10^{-3}$ Torr). The silicon wafer is rotated adjacent the heated NiTi target during deposition of the NiTi (for minimizing compositional variations) so as to fabricate a NiTi film (e.g., about 6 microns thick or in a range of about 2-12 microns thick) with a deposition rate of 0.1 microns per minute.

As seen in FIGS. 1A and 1C, individual web fiches 104 may spaced apart in a regular pattern (e.g., a web fiche pattern 102 of FIG. 1A) so that the un-fenestrated spaces in the web fiche pattern 102 between the individual meshes 104 form areas 108 (also referred to as streets 108) resembling and analogous to streets on a map. Streets 108 may be formed during the DRIE process of creating grooves 160 shown in FIG. 1D. There may be a significant difference in scale between the size of the streets 108 (e.g., 1000 microns) and the widths for fenestrations 106 (e.g., 10 microns). A mask 110 shown in FIG. 1C may be readily formed that takes advantage of the difference in scale between the streets 108 and the fenestrations 106 of the individual web meshes 104. In this fashion, mask 110 may have a spatial alignment resolution of at least 50 microns so that mask 110 covers streets 108 and the longitudinal edges (112 of FIG. 3) of each individual fiche 104 to a depth of about 10 microns or more. It is on these areas covered by mask 110 that first and second NiTi layers 121 and 122 are joined. This joining occurs because sacrificial layer 116 is deposited through mask 110. When mask 110 is removed and second NiTi layer 122 deposited over sacrificial layer 116, NiTi layer 122 will be deposited onto NiTi layer 121 wherever NiTi layer 121 was masked by mask 110 so that a bond 112 (shown in FIG. 2) may be formed between the contacting layers 121 and 122. In alternative embodiments, an additional bonding layer may be deposited to assist in the joining of layers 121 and 122 as will be explained further herein.

Sacrificial layer 116 may be sputter deposited onto first NiTi layer 121 through mask 110. Mask 110 thus prevents the sacrificial (e.g., Cr) layer 116 from depositing on the streets 108 and on the longitudinal edges of each individual mesh 104 of web fiche pattern 102. The entire process of forming a three-dimensional object such as stent cover 114 entails no use of chemical wet etch except a Cr etch of the finished three dimensional object to remove the sacrificial Cr layer 116 and lift-off layer 115. But since layers 121 and 122 are already joined by that time, the wet etching causes no complications. In contrast, the wet etching of the prior art to form the fenestrations was performed prior to the joining of the nitinol layers and thus interfered with this joining through the resulting chemical contamination of the first NiTi layer. All of the process operations up to the final etch of the sacrificial Cr layers, which release the finished three dimensional object, may be carried out in a vacuum without exposure to atmosphere so as to ensure a strong bond 112 between the NiTi layers 121, 122 (e.g., device components 114 of three dimensional device 124). The enhanced quality and strength of the bond 112 compared to other methods such as adhesive, laser welding, or suturing may, for example, provide extra reliability and safety for a stent cover device 124.

Figure 4:
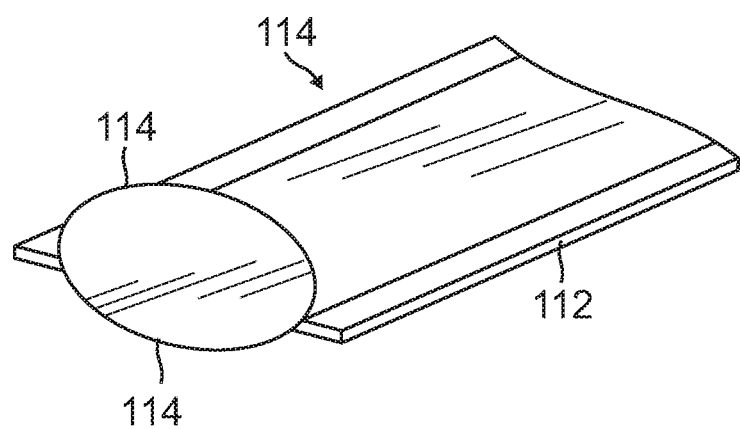
FIG. 4 is a schematic block diagram illustrating a modified structure formed on a silicon wafer substrate, in accordance with an embodiment.

The final etch of the sacrificial Cr layers may produce, as seen in FIG. 3, a device such as a stent cover 114 having a lumen 125 between two NiTi layers that are joined (e.g., by bonds 112) at the edges. The device shown in FIG. 3, although appearing flattened, can be seen to be equivalent topologically to a three dimensional cylinder. Lumen 125 may be enlarged, as seen in FIG. 4 for example, by insertion of a mandrel, and the two NiTi layers (e.g., device components 114) may be shape set (e.g., by annealing) to form a cylindrical stent cover 124 having bonds 112 between the two NiTi layers (e.g., device components 114). Because the bond between the two layers is strong (e.g., approaching the strength of the NiTi material itself) bond 112 can have a width no wider than the thickness of the individual layers. Hence bond 112 may not present a significant obstacle to insertion of stent cover 124 in a catheter for implantation.

Figure 5:
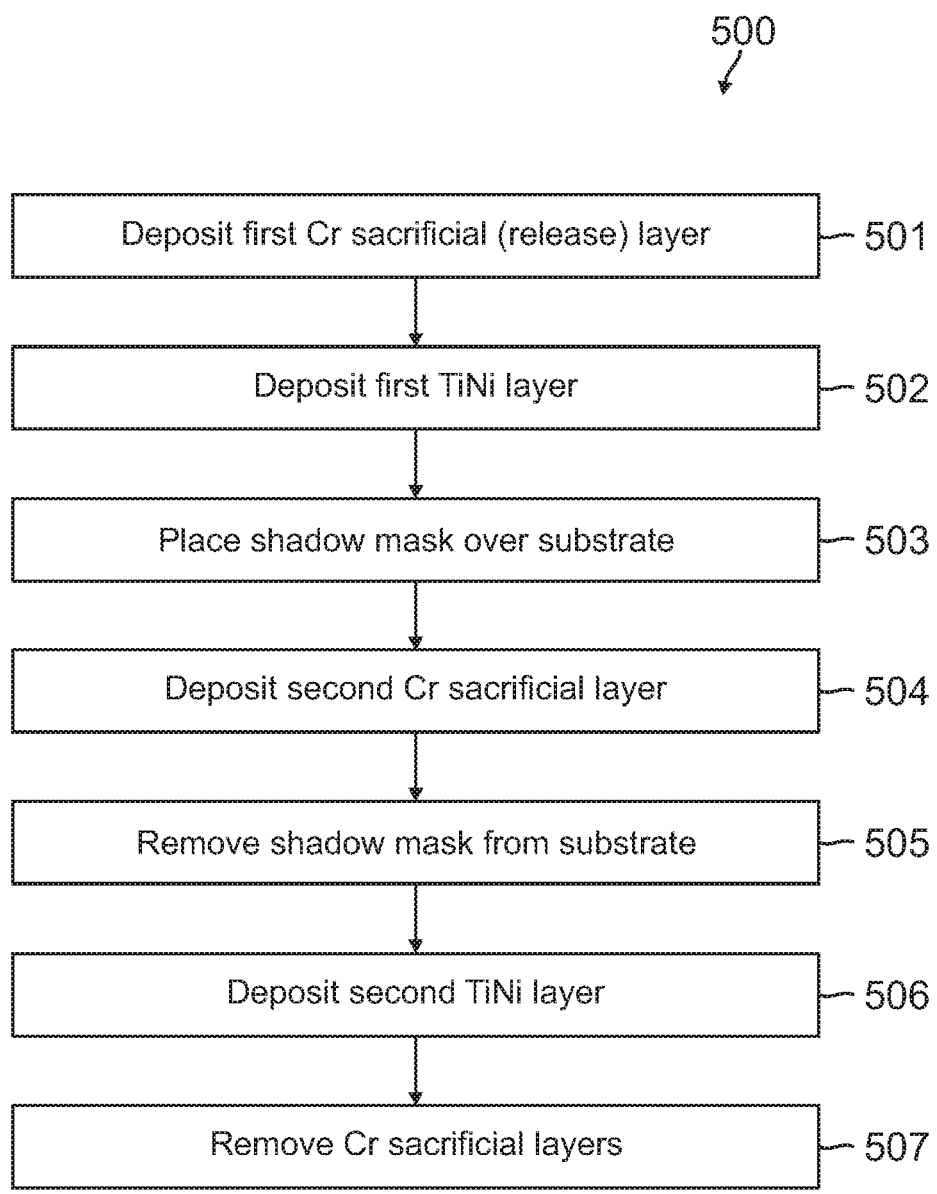
FIG. 5 is a flow diagram illustrating a method for forming a structure on a silicon substrate, in accordance with one or more embodiments.

FIG. 5 illustrates a method 500, in accordance with one or more embodiments, for forming a three dimensional structure on a silicon substrate without wet etching, other than, for example, to release the structure from the substrate. Although description of method 500 refers to production of individual web fiche mesh 104 or single devices 124, it can be seen from FIG. 1A, for example, that many devices 124 can be produced simultaneously using the method of FIG. 5.

At step 501, a first sacrificial layer (e.g., lift-off or release layer 115 shown in FIG. 2) of Cr (or other sacrificial or barrier layers) may be deposited on a silicon substrate (e.g., silicon wafer substrate 100) in a sputtering chamber while the substrate is held at high vacuum or under ultra-high vacuum, using e-beam evaporation or PECVD, for example, as described above. When subsequently etched away, the lift-off layer may release the finished product such as device 114 from the substrate (e.g., silicon wafer substrate 100) and may thus be referred to as a release layer. The lift-off layer may be 1700 to 3000 Angstroms of sputter-deposited chromium.

Prior to the deposition of the lift-off layer, the substrate may first (e.g., before deposition) be prepared in step 501, as described above, by etching (using, for example, dry etching or DRIE) grooves or trenches that will correspond to fenestrations of a web fiche pattern 102 or other surface features that may correspond to structures (e.g., mesh fenestrations) of a finished product such as device 114. Step 501 and subsequent steps 502 through 506 may all be performed while the substrate continues to be held under a vacuum in a sputtering chamber and without removing the vacuum (or removing the substrate wafer or device from the vacuum chamber) until all depositions are completed, even during operations of manipulating a shadow mask, such as at steps 503 and 505 of method 500.

At step 502, a first layer of NiTi (e.g., layer 121 shown in FIG. 2) may be deposited using one or more sputtering or other techniques, examples of which are described above. An example thickness of this first layer (as well as the second layer of NiTi) is 3 to 5 microns.

At step 503, a shadow mask (e.g., mask 110) may be placed over the substrate and the previously deposited layers such as the release layer 115 and NiTi first layer 121. Manipulation (e.g., placing, removing) of the shadow mask may be performed without interrupting the maintaining under vacuum of the substrate and previously deposited layers. The shadow mask may protect covered (or blocked) areas from subsequent deposition of a second Cr sacrificial layer (or other sacrificial or barrier layers). The masked (covered) areas may include portions of the first NiTi layer 121 intended to form a bond 112 with the second NiTi layer 122 so that those same areas (e.g., edges of the individual web fiche mesh 104 to a width of about 10 microns) may be exposed after deposition of the second sacrificial layer. Thus, a mask 110 may be placed with a spatial alignment resolution of 50 microns so that mask 110 covers streets 108 and the edges of the individual web fiche mesh 104 to a width in a range of about 5 microns to about 15 microns.

At step 504, a second sacrificial layer (e.g., layer 116 shown in FIG. 2) of Cr (or other sacrificial or barrier layers) may be deposited on the silicon substrate (e.g., silicon wafer substrate 100) in a sputtering (or vacuum) chamber while the substrate continues to be held at high vacuum or under ultra-high vacuum, using e-beam evaporation or PECVD, for example, as described above.

At step 505, the shadow mask 110 may be removed from the substrate and the accumulated deposited layers. Removal of the shadow mask may be accomplished without removing the vacuum or removing the substrate and accumulated deposited layers from the vacuum.

At step 506, a second layer of NiTi (e.g., layer 122 shown in FIG. 2) may be deposited using one or more sputtering or other techniques, examples of which are described above. At this step, deposition of second layer of NiTi 122 may result in second layer of NiTi 122 bonding to first layer of NiTi 121 at those areas left exposed by the second sacrificial layer 116, forming, for example, bonds 112 at the edges of individual web fiche mesh 104.

At step 507, removal of the sacrificial layers (e.g., first sacrificial or release layer 115 and second sacrificial layer 116) may be performed using a wet etch and may be performed after allowing the vacuum chamber to repressurize or after removing substrate 100 from the vacuum chamber. Etching the sacrificial layers may release the device components 114 from the substrate and may remove interior layers such as second sacrificial layer 116. The etch may comprise soaking silicon substrate wafer 100 and the deposited layers in a solution, for example, of Cr etch, and may create a lumen (e.g., lumen 125 shown in FIG. 3) where sacrificial layers are removed between the first and second NiTi layers that are joined at the edges. Further processing may include shaping device 124 including, for example, shaping device 114 into a more rounded shape, as shown in FIG. 4, by insertion of a mandrel into lumen 125 shown in FIG. 3. With device 114 in the desired shape, the NiTi layers may be crystallized as discussed earlier.

Figure 6:
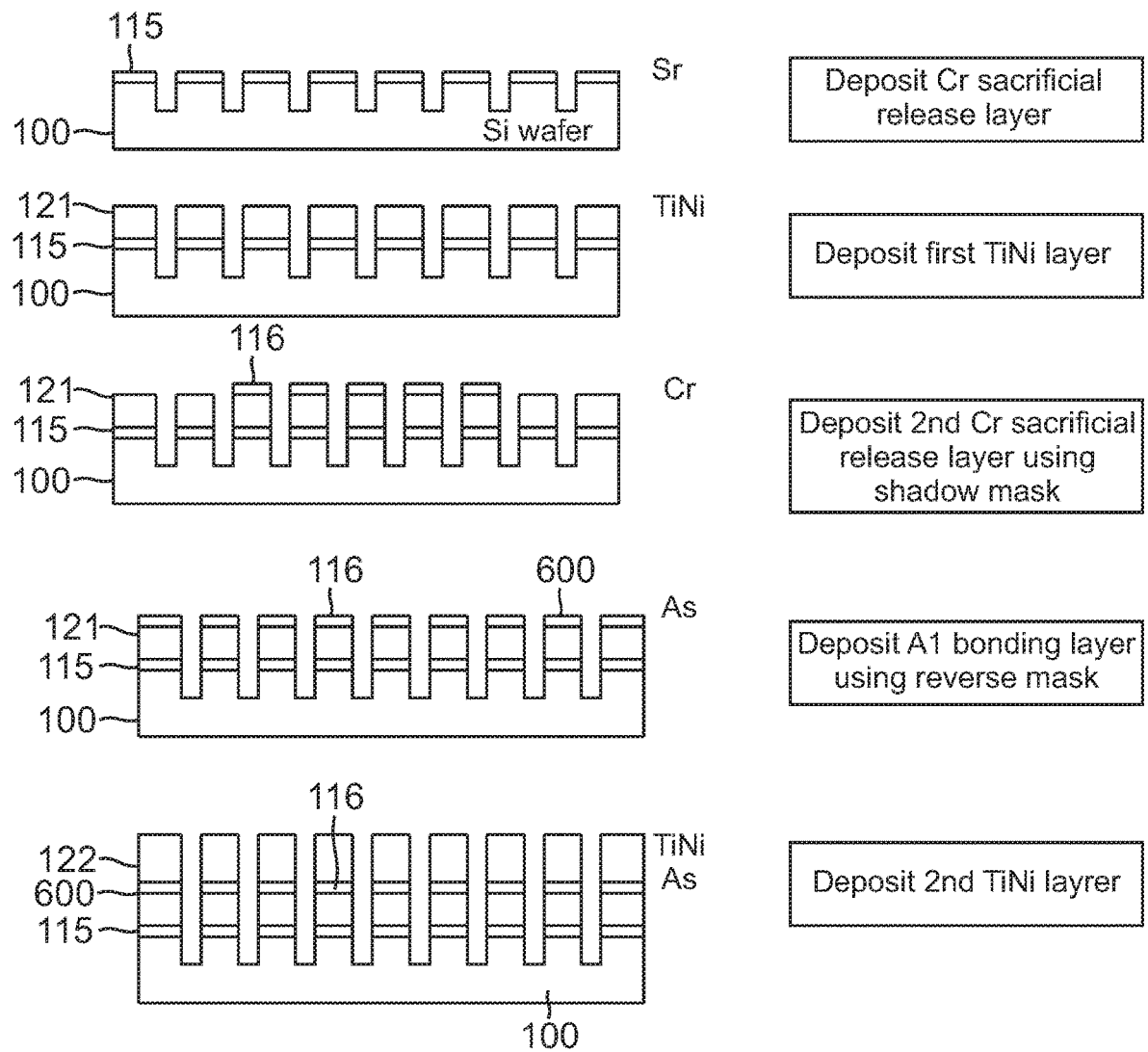
FIG. 6 illustrates steps in the formation of a three-dimensional nitinol structure using an aluminum bonding layer.

It will be appreciated that bonding of one NiTi layer onto another can be problematic in that NiTi readily forms an oxidized surface layer. This surface layer inhibits the bonding of one NiTi layer to another. To prevent formation of this surface oxidized layer requires the first NiTi layer 121 to be maintained in a vacuum or a non-oxidizing environment before second NiTi layer 122 may be bonded to it, which is cumbersome and increases manufacturing costs. For example, mask 110 must be applied and removed while maintaining a high vacuum. The bonding layer discussed below obviates the need to maintain such a vacuum across all the manufacturing steps. Referring now to FIG. 6, manufacturing costs may be lowered as shown in the example manufacturing flowchart. The first three steps are as described previously. In that regard, a lift-off layer 115 is applied to substrate 100, followed by deposition of first NiTi layer 121 and sacrificial layer 116. But before the second NiTi layer 122 is deposited, an aluminum bonding layer is applied using a reverse mask (not illustrated). This reverse mask is (as implied by the name), the complement of mask 110 used to form sacrificial layer 116. In other words, the reverse mask covers sacrificial layers 116 and exposes the uncovered areas of first NiTi layer 121. Aluminum may then be sputtered through the reverse mask to form bonding layer 600. Since bonding layer 600 is applied, first NiTi layer 121 may be exposed to the atmosphere between the masking with mask 110 and the subsequent masking with the reverse mask. In this fashion, manufacturing costs are lowered in that the applications of the masks is greatly aided by performing the mask applications outside of the vacuum chamber using, for example, conventional semiconductor pick-and-place equipment. After application of bonding layer 600, second NiTi layer 122 may be sputter deposited as discussed earlier. The wafer 100 may then be heated to approximately 500 to 600 degrees prior to removal of the lift-off and sacrificial layers. Such heating partially melts the aluminum, which then becomes very reactive despite the formation of some aluminum oxides. The molten un-oxidized aluminum is very reactive and chemically bonds to the NiTi layers, resulting in a very secure bond, despite the formation of an oxidized NiTi surface on the first NiTi layer.

Figure 7A:
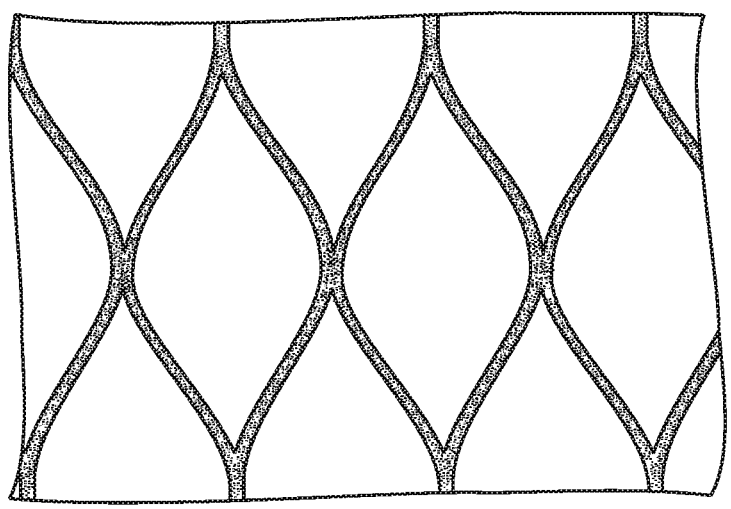
FIG. 7A illustrates expanded diamond-shaped fenestrations in a nitinol stent cover.
Figure 7B:
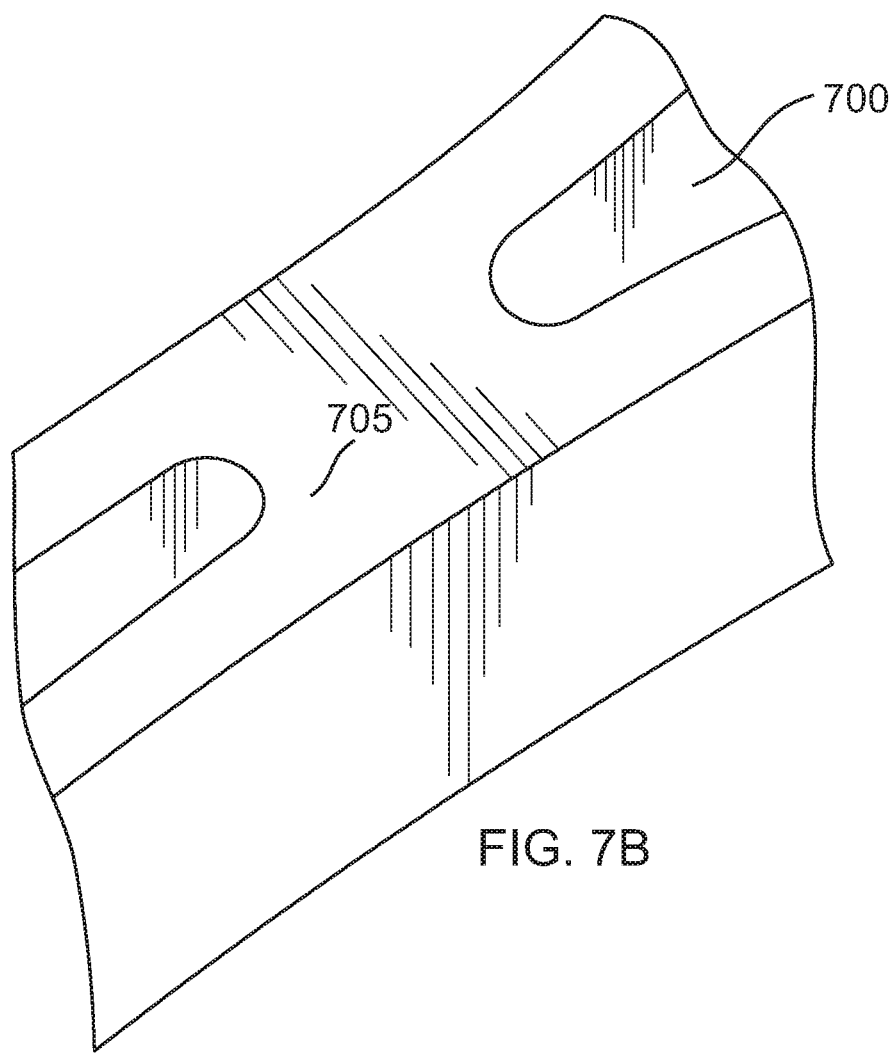
FIG. 7B is a close-up view of the longitudinal intersection between adjacent fenestrations in FIG. 7A.

Regardless of whether an aluminum bonding layer is used, the resulting stent cover is quite advantageous over conventional wire mesh approaches. For example, a conventional wire mesh to function as a flow diverter stent cover uses a wire of at least 30 to 40 microns in diameter. Such a relatively thick wire must weave up or under adjacent strands to form the desired mesh. But the mesh from the techniques described herein is planar with regard to the wire intersections. In that regard, the columnar fenestrations may be expanded into diamond shapes having a length of approximately 300 microns and a width of approximately 150 microns. In contrast, the resulting wire forming the diamond-shaped fenestrations is only 5 to 20 microns in thickness. Each "corner" of the diamond-shaped fenestration is thus relatively flat such that a null region with regard to fluid flow is formed at each corner. This may be better appreciated with regard to FIG. 7A, which shows the diamond-shaped fenestrations that result upon expansion of the columnar fenestrations 104 shown earlier. As shown in the close-up view in FIG. 7B for the adjacent longitudinal ends of two diamond-shaped fenestrations, the wire mesh forms regions 700 and 705 in the interstices of the resulting flat wire mesh that are advantageously conducive to the desired clotting process so that flow diversion of aneurysm is safely achieved. Such interstices are absent in a conventional wire mesh cover because of the weaving of the relatively coarse wire. In contrast, the width W for the wire mesh of FIG. 7B may be 10 microns or less.

As discussed earlier, DC sputtering of NiTi layers 121 and 122 is problematic in that the resulting nitinol may be too brittle due to an undesirable columnar crystalline structure being formed upon deposition. Alternatively, the deposition may be amorphous but possess such tensile strain that it buckles or even cracks the semiconductor substrate surface. To provide high-quality film and solve this prior-art issues, DC sputtering may be performed using the following parameters. In particular, the Ar pressure in the vacuum chamber should be 3 milli Torr or less, more preferably 2 milli Torr or less. The sputtering power should be at least 1 kilowatt and more preferably at least 2 kilowatts. Finally, the distance between the sputtering target and the semiconductor substrate surface should be between 2 and 3.5 inches.

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. A method comprising:
    deep reactive ion etching a pattern of grooves on a surface of a semiconductor substrate, the grooves corresponding to fenestrations in a desired three-dimensional nitinol structure;
    depositing a lift-off layer on the grooved semiconductor substrate surface;
    depositing a first NiTi layer over the lift-off layer;
    depositing a sacrificial layer through a shadow mask to partially cover the first NiTi layer, the sacrificial layer corresponding to a lumen in the desired three-dimensional nitinol structure;
    sputter depositing an aluminum bonding layer onto the first NiTi layer through a reverse mask prior to deposition of a second NiTi layer, the reverse mask being approximately a reverse image of the shadow mask; and
    depositing the second NiTi layer over the sacrificial layer and the aluminum bonding layer.

2. The method of claim 1, further comprising:
    removing the lift-off layer and the sacrificial layer so that the first and second NiTi layers are separated from the semiconductor substrate and so that the lumen is formed in the resulting three-dimensional nitinol structure.

3. The method of claim 1, wherein depositing the lift-off layer comprises depositing a copper or chromium lift-off layer.

4. The method of claim 1, wherein depositing the sacrificial layer comprises depositing a chromium sacrificial layer.

5. The method of claim 1, further comprising heating the aluminum bonding layer so that the aluminum bonding layer bonds the first NiTi layer to the second NiTi layer.

6. The method of claim 2, further comprising inserting a mandrel into the lumen of the three-dimensional nitinol structure, and heating the three-dimensional nitinol structure while it is on the mandrel to crystallize the first and second nitinol layers.

7. The method of claim 6, wherein the three-dimensional nitinol structure is a flow diverter stent cover, the method further comprising covering a flow diverter stent with the flow diverter stent cover.

\* \* \* \* \*